US012559762B2

(12) United States Patent
Augustine et al.

(10) Patent No.: US 12,559,762 B2
(45) Date of Patent: **\*Feb. 24, 2026**

(54) METHODS FOR PRODUCING TRANSFORMED PLANTS

(71) Applicant: FRAUNHOFER-GESELLSCHAFT ZUR FÖRDERUNG DER ANGEWANDTEN FORSCHUNG E.V., Munich (DE)

(72) Inventors: Sruthy Maria Augustine, Aachen (DE); Anoop Vadakan Cherian, Giessen (DE); Kerstin Seiling, Lippetal (DE); Nicole Raven, Giessen (DE); Stefano Di Fiore, Neuss (DE); Stefan Schillberg, Aachen (DE); Ulrich Commandeur, Aachen (DE)

(73) Assignee: FRAUNHOFER-GESELLSCHAFT ZUR FÖRDERUNG DER ANGEWANDTEN FORSCHUNG E.V., Munich (DE)

( \* ) Notice: Subject to any disclaimer, the term of this patent is extended or adjusted under 35 U.S.C. 154(b) by 118 days.

This patent is subject to a terminal disclaimer.

(21) Appl. No.: 18/026,102

(22) PCT Filed: Sep. 15, 2021

(86) PCT No.: PCT/EP2021/075393
§ 371 (c)(1),
(2) Date: Mar. 13, 2023

(87) PCT Pub. No.: WO2022/058392
PCT Pub. Date: Mar. 24, 2022

(65) Prior Publication Data
US 2023/0357783 A1 Nov. 9, 2023

(30) Foreign Application Priority Data

Sep. 16, 2020 (EP) ..................................... 20196444

(51) Int. Cl.
*C12N 15/82* (2006.01)

(52) U.S. Cl.
CPC ................................. *C12N 15/8206* (2013.01)

(58) Field of Classification Search
None
See application file for complete search history.

(56) References Cited

U.S. PATENT DOCUMENTS

2019/0071695 A1\* 3/2019 Wagner .................. A61B 18/26

FOREIGN PATENT DOCUMENTS

| AU | 2013257385 B2 | \* | 11/2013 |
| EP | 1225228 A2 | | 12/2001 |
| EP | 3392339 A1 | | 10/2018 |

OTHER PUBLICATIONS

Rukmana et al (Enzyme-Assisted Photoinjection of Megadalton Molecules into Intact Plant Cells Using Femtosecond Laser Amplifier. Nature p. 3-9, 2019). (Year: 2019).\*
Lakshmanan et al (Rapid and Efficient Gene Delivery into Plant Cells Using Designed Peptide Carriers. Biomacromolecules, p. 10-16, 2012). (Year: 2012).\*
Schinkel et al (Infrared Picosecond Laser for Perforation of Single Plant Cells. Biotechnology and Bioengineering, p. 244-248, 2008). (Year: 2008).\*
Sakai et al (Combining laser-assisted microdissection (LAM) and RNA-seq allows to perform a comprehensive transcriptomic analysis of epidermal cells of Arabidopsis embryo. Plant Methods. p. 1-12, 2018). (Year: 2018).\*
Tang et al (Efficient delivery of small interfering RNA to plant cells by a nanosecond pulsed laser-induced stress wave for post-transcriptional gene silencing. Plant Science. p. 376-381, 2006). (Year: 2006).\*
International Preliminary Report on Patentability for PCT/EP2021/075388 mailed Mar. 21, 2023.
Mollie Schubert et al: "Fluorescently labeled tracrRNA provides efficient genome editing while allowing cellular microscopy and FACS analysis", Jan. 1, 2017 (Jan. 1, 2017), Retrieved from the internet on May 7, 2019 as: URL: http://sfvideo.blob.core.windows.net/sitefinity/docs/default-source/application-note/alt-r-crispr-cas9-tracrrna-atto-550-app-note.pdf?sfvrsn=72b03707_4.
Tang Wei et al: "Efficient delivery of small interfering RNA to plant cells by a nanosecond pulsed laser-induced stress wave for post-transcriptionalgene silencing", Plant Science (2006) 171(3):375-381.
Shan Li et al., "HRM—facilitated rapid identification and genotyping of mutations induced by CRISPR/Cas9 mutagenesis in rice", Crop Breeding and Applied Biotechnology (2018) 18: 184-191.
Thamalampudi Venkata Reddy et al., "Development of TILLING by sequence platform towards enhanced leaf yield in tobacco", Industrial Crops and Products (2012) 40: 324-335.
Helga Schinkel et al., "Infrared Picosecond Laser for Perforation of Single Plant Cells", Biotechnology and Bioengineering, (2008) 99(1): 244-248.

\* cited by examiner

*Primary Examiner* — Wayne Zhong
(74) *Attorney, Agent, or Firm* — Biotech Beach Law PC; Raymond Wagenknecht

(57) ABSTRACT

Methods for highly efficient and fast generation of transformed plants, highly efficient, mild and fast generation methods for introducing a biomolecule into an intact plant cell by a laser-assisted transfection method, and the regeneration of cell lines, whole tissues or organisms thereof.

17 Claims, 8 Drawing Sheets

Specification includes a Sequence Listing.

A
Before ablation

A'
After ablation

A"

A
Epifluorescence images

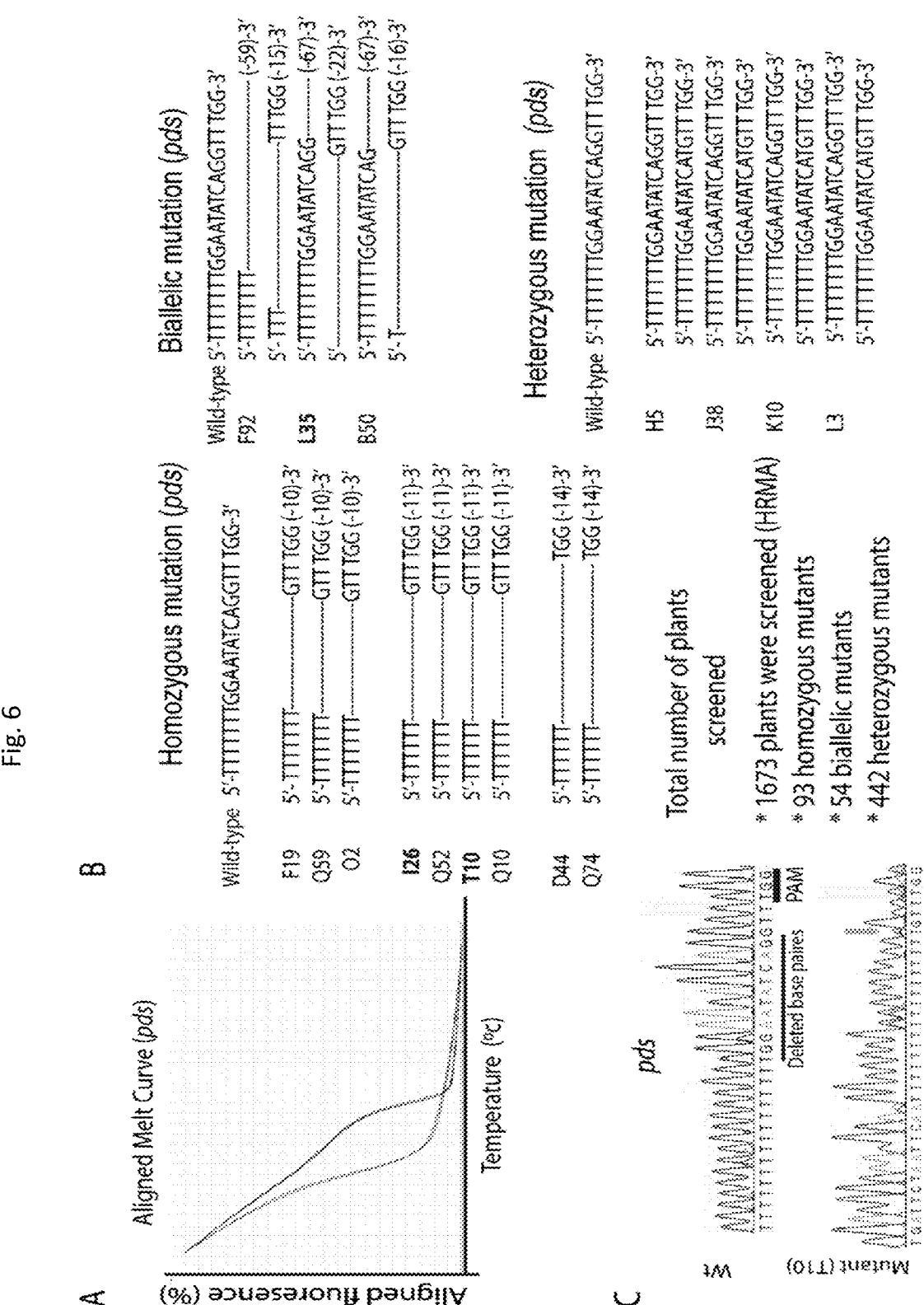

Homozygous mutation (pds)

Wild-type 5'-TTTTTTTTGGAATATCAGGTT TGG-3'

| | |
|---|---|
| F19 | 5'-TTTTTTTT————GTT TGG (-10)-3' |
| Q59 | 5'-TTTTTTTT————GTT TGG (-10)-3' |
| O2 | 5'-TTTTTTTT————GTT TGG (-10)-3' |
| I26 | 5'-TTTTTTTT————GTT TGG (-11)-3' |
| Q52 | 5'-TTTTTTTT————GTT TGG (-11)-3' |
| T10 | 5'-TTTTTTTT————GTT TGG (-11)-3' |
| Q10 | 5'-TTTTTTTT————GTT TGG (-11)-3' |
| D44 | 5'-TTTTTTTT————TGG (-14)-3' |
| Q74 | 5'-TTTTTTTT————TGG (-14)-3' |

Biallelic mutation (pds)

Wild-type 5'-TTTTTTTTGGAATATCAGGTT TGG-3'

| | |
|---|---|
| F92 | 5'-TTTTTTTT————(-59)-3' |
| | 5'-TTT————TTTGG (-15)-3' |
| L35 | 5'-TTTTTTTTGGAATATCAGG————(-67)-3' |
| | 5'————GTT TGG (-22)-3' |
| B50 | 5'-TTTTTTTTGGAATATCAG————(-67)-3' |
| | 5'-T————GTT TGG (-16)-3' |

Heterozygous mutation (pds)

Wild-type 5'-TTTTTTTTGGAATATCAGGTT TGG-3'

| | |
|---|---|
| H5 | 5'-TTTTTTTTGGAATATCAGGTT TGG-3' |
| | 5'-TTTTTTTTGGAATATCAGGTT TGG-3' |
| J38 | 5'-TTTTTTTTGGAATATCAGGTT TGG-3' |
| | 5'-TTTTTTTTGGAATATCATGTT TGG-3' |
| K10 | 5'-TTTTTTTTGGAATATCATGTT TGG-3' |
| | 5'-TTTTTTTTGGAATATCAGGTT TGG-3' |
| L3 | 5'-TTTTTTTTGGAATATCAGGTT TGG-3' |
| | 5'-TTTTTTTTGGAATATCATGTT TGG-3' |

Total number of plants screened

* 1673 plants were screened (HRMA)
* 93 homozygous mutants
* 54 biallelic mutants
* 442 heterozygous mutants

METHODS FOR PRODUCING TRANSFORMED PLANTS

CROSS REFERENCE TO RELATED APPLICATIONS

This is a US national phase application under 35 U.S.C. § 371 of international PCT application No. PCT/EP2021/075393, filed Sep. 15, 2021, which claims priority to European patent application no. 20196444.2, filed Sep. 16, 2020; the content of each is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing as file "PCTEP2021075393_SEQ-ID-ASCII" created on 13 Mar. 2023, filed on 13 Mar. 2023 and having a size of 8 Kilobytes.

The sequence listing contained in this ASCII formatted document forms part of the specification and is herein incorporated by reference in its entirety.

TECHNICAL FIELD

The technology provided herein relates to methods for highly efficient and fast generation of transformed plants. Furthermore, the technology provided herein relates to highly efficient, mild and fast generation methods for introducing a biomolecule into an intact plant cell by a laser-assisted transfection method, and the regeneration of cell lines, whole tissues or organisms thereof.

BACKGROUND

One general object of modern biotechnology is to genetically engineer crop plants by introducing new genetic information or simply biomolecules into plants. Plants with new traits, such as insect resistance or herbicide resistance, and artificial manipulations of the agronomic qualities of the crop product, can be generated once recombinant genes are introduced into plant lines.

The first widely used plant genetic engineering technique was based on the natural ability of the soil-dwelling microorganism *Agrobacterium tumefaciens* to introduce a portion of its DNA into a plant cell as a part of the normal pathogenic process. If a foreign gene is inserted into the bacteria in certain ways, the *Agrobacterium* can be used to transfer the foreign gene into a plant. *Agrobacterium* transformation techniques have been developed for a number of plants, mostly dicotyledonous, but the usefulness of the technique has varied from plant species to species. *Agrobacterium*-based transformation systems are limited because they require cell or tissue culture and plant regeneration techniques. Plant lines vary in their amenability to tissue culture and regeneration methods. Furthermore, DNA transferred via *Agrobacterium* is less likely to undergo any major rearrangements than is DNA transferred via direct delivery, and it integrates into the plant genome often in single or low copy numbers.

A further technique for creating transformed plants includes bombarding a plant cell with accelerated particles which carry genetic information. The first indication of the utility of this technique was a demonstration that DNA constructs could be coated onto tungsten particles and accelerated into onion skin, where the genes were transiently expressed, as is described in the specification of U.S. Pat. No. 4,945,050.

However, such biolistic delivery methods furthermore are technically challenging, require sophisticated and expensive equipment, and largely depend on sterile tissue culturing steps for generating genetically modified and genome-edited organisms. The dependence on sterile tissue culture techniques, which typically involve cell dedifferentiation by hormones, not only limits the application of particle bombardment, but also increases the chances to acquire undesired epigenetic effects and somaclonal variations in the resulting regenerated organisms. This then can make additional breeding steps necessary, which are time consuming and costly.

Another problem associated with many delivery methods, and particularly with particle bombardment, is that delivery of the cargo is limited to a few cells only, i.e. that the overall efficiency is low. The few cells that have received the cargo are present in between a large number of cells that have not received the cargo. When taking samples for analysis, the percentage of cells that are affected by the treatment is usually not known, which can significantly obscure and confound the analysis. For the same reasons, the regeneration of cell lines, whole tissue or organisms from the treated cells is laborious and time consuming. Many experiments are performed, and the treated cells are incubated over prolonged periods of time to ensure that at least a few events, i.e. genetically modified cell lines, whole tissues or organisms, are obtained.

Thus, there is a need in the field for novel methods that offer simpler and more effective ways of delivering biomolecules like nucleic acids and/or polypeptides into differentiated intact plant cells with a cell wall for a wide variety of plant species, and in particular to reduce the workload and increase the overall efficiency for generating transformed plants from these transfected cells.

SUMMARY OF THE DISCLOSURE

The present disclosure pertains to methods for highly efficient, mild and fast introducing biomolecules into intact and differentiated plant cells, in particular to produce transformed plants.

In a first aspect, the present disclosure pertains to methods of producing a transformed plant by introducing an expression vector into an intact plant cell with a laser-assisted transfection method comprising the steps of:

- (i) providing an intact plant or a plant explant isolated by any organ and tissue of a plant and comprising intact plant cells or an isolated plant cell;
- (ii) providing an expression vector and a selectable marker;
- (iii) delivering said expression vector and the selectable marker into the plant cell by a laser-assisted transfection method, wherein the cell or tissue is surrounded by a liquid and the laser focal point is in the liquid adjacent to the cell wall and not directly in contact with the cell wall;
- (iv) identifying the cells transfected with the expression vector; and/or
- (v) selecting the cells transfected with the expression vector and regenerating the cells to intact plantlets by growing in and/or on a growth media.

In a second aspect, the present disclosure pertains to methods for introducing a biomolecule into an intact plant cell by a laser-assisted transfection method comprising the steps of:

(i) providing a plant explant isolated by any organ and tissue of a plant and comprising intact plant cells or an isolated plant cell and selectable marker;

(ii) providing a biomolecule and a selectable marker;

(iii) delivering said biomolecule and the selectable marker into the plant cell by a laser-assisted transfection method, wherein the cell or tissue is surrounded by a liquid and the laser focal point is in the liquid adjacent to the cell wall and not directly in contact with the cell wall.

In particular, the methods according to the present disclosure may solve the following technical problems related to DNA-free genome editing in plants:

facilitates the introduction of biomolecules like expression cassettes, expression vectors and/or polypeptides in intact plant cells and shows high efficiency compared to existing methods.

it is gentle and therefore harnesses a high efficiency of plant regeneration from plant leaf explants compared to existing methods within a short period of time.

In particular, with the methods according to the present disclosure pre-assembled RNP complexes could also be delivered through the cell wall into the cell by a laser-assisted transfection method.

Furthermore, the methods according to the present disclosure enables the use of "cells obtained from non-sterile environment and/or provided under non-sterile environment". In the prior art it is mentioned that cells grown in sterile tissue culture differ from cells obtained from non-sterile environments in many aspects. Cells cultivated in sterile tissue culture are dividing, and often they are (partly) dedifferentiated, treated with growth hormones, and generally have different intracellular states (metabolism, gene expression, . . . ). Phenomena such as soma-clonal variation, epigenetic changes, activation of transposons, promotor methylation, gene activation/deactivation, are all well known in the art and are of concern in breeding programs, genetic engineering and genome editing.

Many species are difficult to maintain in tissue culture, and often this is restricted to particular cultivars only. For many reasons it is therefore highly desirable to reduce the amount of tissue culture as much as possible or to avoid it altogether.

The method of the present disclosure may comprise a sequential application of non-invasive techniques including 1. laser-assisted transfection of e.g. of biomolecules like expression cassettes, expression vectors and/or polypeptides in intact plant cells, 2. optically and/or non optically aided selection and excision of transfected plant cells within plant tissue explants, 3. regeneration of plantlets and 4. genetic profiling and screening of transfected cells by e.g. High Resolution Melt Analysis (HRMA).

The method of the present disclosure are largely advantageous over contemporary methods, such as particle bombardment, electroporation, PEG-mediated transfection and microinjection because it overcomes all the collective limitations of these alternative methods.

Unlike PEG-mediated transfection, the present methods allows the direct introduction of biomolecules into intact plant cells rather than protoplasts, thus reducing the time required for regeneration and making the method accessible in species that cannot yet regenerate from protoplasts. Unlike other physical delivery techniques, the present methods are gentle because the fine-tuned laser irradiation does not affect cell viability and preserves a larger population of intact transfected cells, making it easier to isolate transfected cells and tissue segments for regeneration.

One of the most important aspects according to the present methods is the flexibility because the principles of the methods are universally applicable to any explant of any plant species that can be regenerated in tissue culture. The methods are particularly advantageous for the development of transformed plants of different species in a very short period, particularly for those species that cannot be regenerated via protoplasts or that are particularly difficult to transfect with current methods.

Efficient delivery of biomolecules like expression vectors is required for producing transformed plants, and the methods of the present disclosure are mainly based on laser-assisted transfection method, wherein the cell is surrounded by a liquid and the laser focal point is in the liquid adjacent to the cell wall and is not directly in contact with the cell wall.

One of the most important aspects of the present disclosure is the production of transformed plants/crops of different species in a very short period of time, potentially any plant species that can be regenerated in tissue culture, because the principle of the method is universally applicable to any plant explant including dicots and monocots.

Before the disclosure is described in detail, it is to be understood that this disclosure is not limited to the particular component parts of the process steps of the method described. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 6: A) Representative image showing the high-resolution melt analysis of a pds mutant (line T10) generated and selected with the method of the present invention. B) Sequence alignments of genome-edited mutants. C) Representative chromatogram of wild-type and pds mutant plant (line T10).

DETAILED DESCRIPTION OF THE DISCLOSURE

Figure 1:
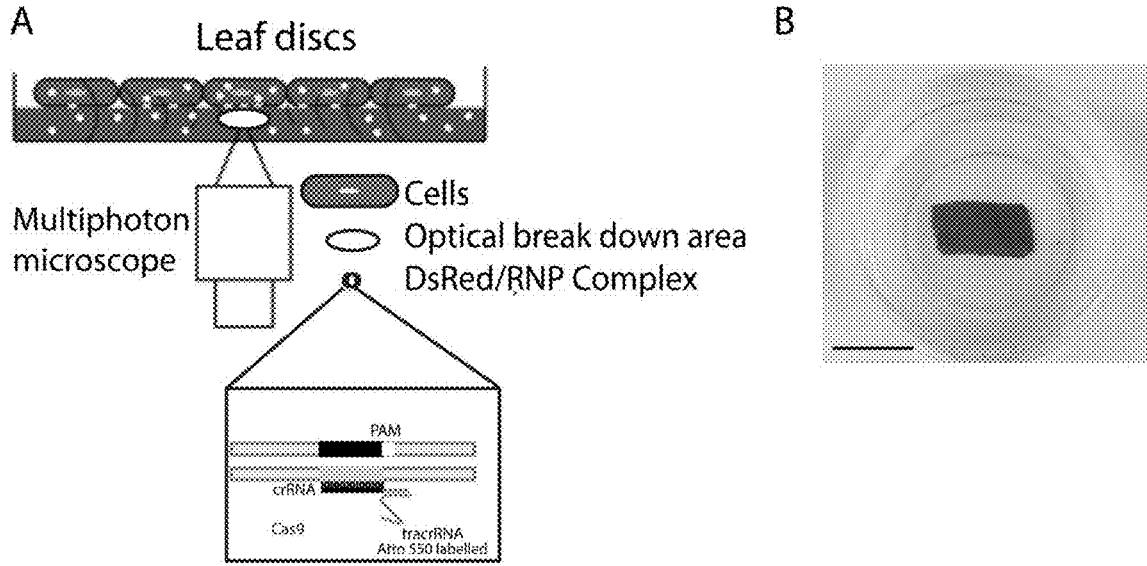
FIG. 1: A) Schematic representation of the laser setup. B) Representative leaf sample used for DsRed/RNP introduction. Scale bar=1 cm.

The present disclosure pertains to the generation of transformed plants, in particular by introducing biomolecules like expressions vectors into an intact plant cell, selection of the transfected cells and regeneration of whole plants thereof. The biomolecules are delivered through the plant cell wall by a laser-assisted transfection method, wherein the cell is surrounded by a liquid and the laser focal point is in the liquid adjacent to the cell wall and not directly in contact with the cell wall and/or the plant cell in general. In particular, the biomolecule is a nucleic acid like an expression vector/expression cassette, a polypeptide and/or combinations thereof like a pre-assembled ribonucleoprotein complexes (RNP)—such as a Cas9/gRNA RNP complex.

In contrast to the procedures of the prior art of delivering biomolecules by protoplast transfection, with the present methods eukaryotic cells like plant cells (i.e. suspension cells, calli, leaves, stems, cotyledons, pollen, etc.) can be readily edited without the need of going through the protoplast stage. As not all plant species are amenable to protoplasting, and regeneration of whole plants from protoplasts is technically difficult, this is a major improvement that greatly simplifies and most importantly extends the use of cell transfection to basically any plant species that can regenerate from tissue culture.

Furthermore, the method of the present disclosure does not require the use of an activated surface for shuttling a foreign cargo into a plant cell. In contrast, the laser in the methods according to the present disclosure is focused in a point of a solution surrounding the plant cell wherein the cargo is suspended or dissolved.

The laser-based method of the present disclosure is not meant to induce abrasion or direct perforation in the wall and membrane of a plant cell, but rather a transient permeabilization of these two cell barriers. The technical problem to be solved is a gentle way to transfer a cargo to an intact plant cells in order to ensure a high rate of success in regeneration of genetically transformed plants. This is achieved by precisely focusing the laser beam to a certain distance from the intact plant cell in a solution surrounding the plant cells. Thus, in the methods according to the present disclosure the plant cell remains intact after laser treatment.

In an advantageous embodiment, the present disclosure pertains to a method of producing a transformed plant by introducing an expression vector into an intact plant cell with a laser-assisted transfection method comprising the steps of:

(i) providing a plant explant isolated by any organ and tissue of a plant and comprising intact plant cells or an isolated plant cell and selectable marker;

(ii) providing a biomolecule and a selectable marker;

(iii) delivering said biomolecule and the selectable marker into the plant cell by a laser-assisted transfection method, wherein the cell or tissue is surrounded by a liquid and the laser focal point is in the liquid adjacent to the cell wall and not directly in contact with the cell wall.

The method according to the present description may comprise the further step of screening of the transformed plants and/or the transfected plant cells, in particular by genetic characterization.

An important aspect of the present disclosure is that a biomolecule like an expression vector/expression cassette is delivered into the plant cell by a laser-assisted transfection method, wherein the cell is surrounded by a liquid and the laser focal point is in the liquid adjacent to the cell wall and not directly in contact with the cell wall and/or the plant cell.

The term "transfection" is used to refer to the uptake of a foreign biomolecule like a nucleic acid and/or a polypeptide by a cell. A cell has been "transfected" when an exogenous biomolecule like DNA has been introduced inside the cell membrane.

The term "biomolecule" includes macromolecules (or polyanions) such as polypeptides, proteins, carbohydrates, lipids, and polynucleotides (nucleic acids) like DNA or RNA, as well as small molecules such as primary metabolites, secondary metabolites and natural products. In particular, the biomolecule transfected/introduced into an intact plant cell with the laser-assisted transfection method of the present disclosure is an expression vector and/or an expression cassette.

The term "polynucleotide" corresponds to any nucleic acid of any length and any sequence, comprising single-stranded and double-stranded DNA and RNA molecules, including regulatory elements, structural genes, groups of genes, vectors like plasmids, whole genomes and fragments thereof. In particular, the polynucleotide introduced to an intact plant cell is an expression cassette/expression vector.

As used herein, the term "nucleic acid" includes a single or double-stranded polymer of deoxyribonucleotide or ribonucleotide bases read from the 5' to the 3' end. The "nucleic acid" may also optionally contain non-naturally occurring or altered nucleotide bases that permit correct read through by a polymerase and do not reduce expression of a polypeptide encoded by that nucleic acid. The term "nucleotide sequence" or "nucleic acid sequence" refers to both the sense and antisense strands of a nucleic acid as either individual single strands or in the duplex. The term "ribonucleic acid" (RNA) is inclusive of RNAi (inhibitory RNA), dsRNA (double stranded RNA), siRNA (small interfering RNA), mRNA (messenger RNA), miRNA (micro-RNA), tRNA (transfer RNA, whether charged or discharged with a corresponding acylated amino acid), and cRNA (complementary RNA) and the term "deoxyribonucleic acid" (DNA) is inclusive of cDNA and genomic DNA and DNA-RNA hybrids. The words "nucleic acid segment", "nucleotide sequence segment", or more generally "segment" will be understood by those in the art as a functional term that includes both genomic sequences, ribosomal RNA sequences, transfer RNA sequences, messenger RNA sequences, operon sequences and smaller engineered nucleotide sequences that express or may be adapted to express, proteins, polypeptides or peptides.

The term "expression cassette" as used herein includes a polynucleotide sequence encoding a polypeptide to be expressed and sequences controlling its expression such as a promoter and optionally an enhancer sequence, including any combination of cis-acting transcriptional control elements. The sequences controlling the expression of the gene, i.e. its transcription and the translation of the transcription product, are commonly referred to as regulatory unit. Most parts of the regulatory unit are located upstream of coding sequence of the gene and are operably linked thereto. The expression cassette may also contain a downstream 3' untranslated region comprising a polyadenylation site. The regulatory unit of the invention is either operably linked to the gene to be expressed, i.e. transcription unit, or is separated therefrom by intervening DNA such as for example by the 5'-untranslated region of the heterologous gene. Preferably, the expression cassette is flanked by one or more suitable restriction sites in order to enable the insertion of the expression cassette into a vector and/or its excision from a vector. Thus, the expression cassette according to the present invention can be used for the construction of an expression vector, in particular a plant expression vector.

The term "expression vector" as used herein includes an isolated and purified DNA molecule which upon transfection into an appropriate host cell provides for expression of a recombinant gene product within the plant host cell. In addition to the DNA sequence coding for the recombinant or gene product (gene of interest) the expression vector comprises regulatory DNA sequences that are required for an efficient transcription of the DNA coding sequence into mRNA and for an efficient translation of the mRNAs into proteins in the host cell line. The terms "host cell" or "host cell line" as used herein include any cells, in particular intact and in particular differentiated plant cells, which are capable of growing in culture and expressing a desired recombinant product protein.

In another embodiment, the biomolecule transfected into the plant cell is a polypeptide or a protein. A polypeptide may be a linear organic polymer consisting of a large number of amino-acid residues bonded together in a chain, forming part of (or the whole of) a protein molecule.

The term "biomolecule" includes also combinations of at least a polypeptide/protein and at least a nucleic acid like a pre-assembled ribonucleoprotein complexes (RNP)—such as a Cas9/gRNA RNP complex. Therefore, the biomolecule could be a combination of at least a polypeptide and at least a nucleic acid like a "CRISPR/Cas" system that refers to a widespread class of bacterial systems for defense against foreign nucleic acid. CRISPR/Cas systems are found in a wide range of eubacterial and archaeal organisms. CRISPR/ Cas systems include type I, II, and III sub-types. Wild-type type II CRISPR/Cas systems utilize an RNA-mediated nuclease, Cas9 in complex with guide and activating RNA to recognize and cleave foreign nucleic acid. Guide RNAs having the activity of both a guide RNA and an activating RNA are also known in the art. In some cases, such dual activity guide RNAs are referred to as a small guide RNA (sgRNA).

The term "selectable marker" confers antibiotic resistance, herbicide resistance, color change, or encodes a polypeptide which can react with a compound to produce a detectable signal. A "selectable marker" or "reporter marker" refers therefore to a nucleotide sequence included in an expression vector/expression cassette that has no therapeutic activity, but rather is included to allow for simpler preparation, manufacturing, characterization or testing of the expression vector/expression cassette. The selectable marker comprised in the expression vector/expression cassette or which is introduced in the intact plant cell in combination with the biomolecule may be any functional element for facilitating subsequent identification and selection of clones of the recombination product under suitable conditions. The selectable marker may encode or is any functional element, such as protein, peptide, RNA, binding site for RNA and proteins, or products that provide resistance to organic or inorganic agents. Examples of selectable markers include, but are not limited to, reporter genes such as -galactosidase (GAL), fluorescent proteins (e.g., GFP, GFP-UV, EFFP, BFP, EBFP, ECFP, EYFP), secreted form of human placental alkaline phosphatase (SEAP), β-glucuronidase (GUS)); resistance genes against antibiotics (e.g. neomycin (G418) or hygromycin resistant gene, puromycin resistant gene), yeast selectable markers leu2-d and URA3, apoptosis resistant genes (e.g. baculoviral p35 gene), and antisenoligonucleotides. The selectable marker may also be present in an additional vector and may be co-transfected with the expression vector and/or the biomolecule of interest into the plant cell.

In particular, the expression vector/expression cassette in a method of the present disclosure comprises a marker gene. As mentioned above, a marker is a detectable genetic trait or segment of DNA that can be identified and tracked. A marker gene typically serves as a flag for another gene, sometimes called the target gene. A marker gene is typically used with a target gene being used to transform target cells. Target cells that heritably receive the target gene can be identified by selecting for cells that also express the marker gene. The marker gene is near enough to the target gene so that the two genes (the marker gene and the target gene) are genetically linked and are usually inherited together.

The term "selectable marker" as used herein includes also visual markers or visual marker molecules that can be detected optically due to their light absorbing and emitting properties, include but not limited to dyes, fluorescent dyes, fluorescent proteins, quantum dots. An enzyme that produces a dye or fluorescent dye or a pigment by converting an endogenous substrate or upon addition of a substrate is also considered a visual marker. Examples include e.g. β-glucuronidase, β-galactosidase, anthocyanidin synthase, luciferase, phytoene desaturase and others. In the context of this invention, a transcription factor or inducer of gene expression, that leads to the expression of an endogenous gene that subsequently causes a change in the optical properties of the cell(s), is also considered a visual marker. Examples are transcription factors from the MYC, MYB, and WD40 families, such as MdMYB1, MdMYB10 and MdMYBA from apples or *Arabidopsis* PAP1 (production of anthocyanin pigment 1). In advantageous embodiments, the ribonucleic acid of the pre-assembled ribonucleoprotein (RNP)-complex is fluorescent labeled e.g. with a fluorescent dye and/or a fluorescent protein. An example for such a visual marker is ATTO 550 (ATTO-TEC GmbH), a fluorescent label related to the well-known dyes Rhodamine 6G and Rhodamine B. Characteristic features of the label are strong absorption, high fluorescence quantum yield, and high thermal and photo-stability. The dye is moderately hydrophilic. ATTO 550 is a cationic dye. After coupling to a substrate the dye carries a net electrical charge of +1. As supplied ATTO 550 consists of three isomers with practically identical absorption and fluorescence. The fluorescence is excited most efficiently in the range 540-565 nm.

Therefore, the selectable marker provided together with a biomolecule like an expression vector may be a visual marker, encodes a gene for a visual marker, encodes a gene that confers resistance to antibiotic or any other marker that can be used to select transformed plants and/or plant tissue or may be a combination of different selectable markers, and the cells transfected with the expression vector may be identified by microscopy, in particular by fluorescence microscopy and/or by cultivation on solid medium containing appropriate selective agents.

For example, in a method according to the present disclosure the provided expression vector comprises a gene of interest and a selectable marker gene. In some advantageous embodiments, the expression vector could be labeled in addition with a visual marker like a fluorescent dye and/or a fluorescent protein and/or co-transfected with a visual marker like a fluorescent dye and/or a fluorescent protein.

In a further embodiment, the expression vector comprises a gene of interest and a selectable marker gene and the expression vector is delivered into the plant cell in combination with a separate visual marker molecule like a fluorescent protein etc.

Therefore, in an advantageous embodiment the present disclosure pertains also to a method of producing a transformed plant by introducing an expression vector into an intact plant cell with a laser-assisted transfection method comprising the steps of:

(i) providing an intact plant or a plant explant isolated by any organ and tissue of a plant and comprising intact plant cells;

(ii) providing an expression vector comprising a gene of interest and a selectable marker gene and a visual marker molecule;

(iii) delivering said expression vector and the visual marker molecule into the plant cell by a laser-assisted transfection method, wherein the cell or tissue is surrounded by a liquid and the laser focal point is in the liquid adjacent to the cell wall and not directly in contact with the cell wall;

(iv) identifying the cells transfected with the expression vector via the expressed marker gene and/or by microscopy via the visual biomolecule, in particular by fluorescence microscopy;

(v) selecting the cells transfected with the expression vector and regenerating the cells to intact plantlets by growing in and/or on a growth media.

As used herein, the phrase "coding sequence", "encoding sequence", "structural nucleotide sequence" or "structural nucleic acid molecule" refers to a nucleotide sequence that is translated into a polypeptide, usually via mRNA, when placed under the control of appropriate regulatory sequences.

The boundaries of the coding sequence are determined by a translation start codon at the 5'-terminus and a translation stop codon at the 3'-terminus. A coding sequence can include, but is not limited to, genomic DNA, cDNA, EST and recombinant nucleotide sequences.

The term "gene" refers to a DNA sequence that comprises control and coding sequences necessary for the production of a recoverable bioactive polypeptide or precursor. Endogenous gene are those that originate from within an organism, tissue, or cell.

The term "laser-assisted transfection method" includes a method for shuttling biomolecules like nucleic acids and/or polypeptides into intact plant cells of any organ and tissue of a plant, whereby the penetration of the biomolecules is granted by indirect laser irradiation of the said plant cell. Indirect laser irradiation of an intact cell is achieved by focusing a laser beam, in particular the laser focal point by means of a magnifying lens such as an objective of a microscope in the adjacency of the cell and not directly onto the cell i.e. not directly hitting the plant cell, in particular the cell wall of the plant cell.

The term "laser focal point" pertains to a point in space defined by three-dimensional spatial coordinates wherein a laser beam is directed to after passing through a magnifying lens such as but not limited to an objective of a microscope. The laser focal point is affected by the features of the lens such as the curvature and the focal length of the lens and is found at the distance between the front of the lens and the point in space where the laser beam achieves its minimum in diameter. This point in space is the point where the laser is in focus. For the present disclosure, the laser focal point is the point in space where the laser is in focus and it is hitting the liquid medium surrounding the plant cell or plant explant.

The term "adjacency to" pertains to a lateral or vertical distance, i.e. aside, beneath or above the border of the plant cell(s) of 1 to 10 μm and more preferably 3 to 8 μm and even more preferably 2 to 5 μm either laterally or vertically to the plant cell(s), in particular to the plant cell wall. This is achieved for example by: i) layering or submerging a plant explant comprising a plurality of intact plant cells or a suspension of isolated intact plant cells into a liquid deposited onto a transparent support suitable for microscopy; ii) placing this support on a microscope table, iii) engaging an objective to visualize and magnify the plant cells; iv) putting the plant cell in focus, i.e. by obtaining a sharp image of the plant cell sample; and then v) by either selecting a region next to the plant cell in the range of values described above or by defocussing the cell in the vertical direction beneath or above the cell boundaries of the same range of values described above. Those skilled in the art can achieve the exact lateral or vertical displacement of the plant cell in focus by the range of values described above by using the x and y wheels of the microscope table for the lateral displacement or by using the focusing wheels of the microscope for the vertical displacement or if the microscope is equipped with a motorized stage, by changing the horizontal and vertical coordinates of the table by using the software driving the motorized table of the microscope.

The term "liquid" includes any liquid medium including water, any physiological solution including but not limited to physiological saline and any similar physiological solution, any cell culture liquid medium, any buffer including but not limited to phosphate buffer saline, Tris-based buffers, HEPES-based buffers or any other buffer known to those skilled in the art compatible with plant cells and suitable for any molecular biology work.

The intact plant cells comprising a cell wall can be obtained from cell suspensions of single cells or cell aggregates or from tissues such as anthers, callus, cotyledons, embryo, flowers, leaves, pods, roots, seeds and stems or can be part of an intact plant. In an advantageous embodiment, the plant cell is isolated from plant leaves, flowers, seeds, roots or cotyledons before providing the biomolecule.

As used in the present disclosure, "cell", "cell line", and "cell culture" can be used interchangeably and all such designations include progeny. It is also understood that all progeny may not be precisely identical in DNA content, due to deliberate or inadvertent mutations. Mutant progeny that have the same functionality as screened for in the originally transformed cell are included.

The term "isolated" describes any molecule separated from its natural source. The term "isolated" includes material that is substantially or essentially free from components which normally accompany it as found in its native state.

As used herein, the term "intact cells" includes cells characterized by an intact cell membrane and/or cell wall. In particular, if the intact cells are eukaryotic plant cells, the intact plant cells comprise a cell wall. Preferably, an intact cell is collected from and/or comprised within a differentiated tissue. In some advantageous embodiments, an intact plant cell in the methods according to the present disclosure is an intact differentiated plant cell.

As used in this disclosure "differentiated" and "undifferentiated" are relative terms depending on the context in which they are used. Specifically, in reference to a particular type of self-renewing stem cell, the term "undifferentiated" refers back to the same self-renewing stem cell, whereas the term "differentiated" refers to one or more of the relatively mature phenotypes the stem cell can generate—as discernable by morphological criteria, antigenic markers, and gene transcripts they produce. Undifferentiated pluripotent stem cells including iPS cells have the ability to differentiate into all three germ layers. The cells differentiated from them do not, and can readily be recognized by one skilled in the art by morphological criteria. In particular, differentiated plant cells include but are not limited to epidermal and mesophyll cells from cotyledons or leaves, epidermal or vascular cells from roots, epidermal or vascular cells from stems.

The term "plant" includes the plant body, plant organs (for example, leaves, petals, stem, root, rhizome, and seeds), plant tissues (for example, epidermis, phloem, parenchyma, xylem, and vascular bundle), and plant cells. In addition, the term "plant cell" includes cell suspension cultures, embryos, meristematic tissue regions, callus tissues, cells derived from leaves and roots. When plant culture cells are transformed, an organ or individual is regenerated from the transformed cells by a known tissue culture method. These operations are readily performed by those skilled in the art. An example is described below. Firstly, the transformed plant cells are cultured in a sterilized callus inducing medium (containing a carbon source, saccharides, nutrients, vitamins, inorganics, and phytohormones such as auxin and cytokinin), thereby forming a dedifferentiated callus which indefinitely proliferates (callus induction). The formed callus is transferred to a new medium containing a plant growth regulator such as auxin, and further proliferated thereon (subcultivation). When the callus induction is carried out on a solid medium such as agar and subcultivation is carried out in a liquid medium, the respective cultures are efficiently achieved. Secondly, the callus proliferated by subcultivation is cultured under appropriate conditions, thereby inducing re-differentiation of the organ (inductive re-differentiation), and regenerating the plant body. The inductive re-differentiation is achieved by appropriately adjusting the type and amount of the various components of the medium, including plant growth regulators such as auxin and cytokinin, and the carbon source, and the light and temperature. The inductive re-differentiation forms adventitious embryos, adventitious roots, adventitious buds, adventitious foliage, and others, and they are grown into a complete plant body. The plant before being a complete plant body may be stored in the form of, for example, capsulated artificial seeds, dry embryos, lyophilized cells, or tissues. The term "plant explant" as used herein includes any portion of a plant including a plurality of intact plant cells derived by any organ and/or tissue of an organ including but not limited to any seed, embryo, fruit, anther, ovary, leaf, stem, roots and any other tissue or cell type derived from a dicotyledonous or monocotyledonous plant species.

In some advantageous embodiments, the methods according to the present disclosure comprise a multiplex genome modifying formulation (multiplexing) for introducing at least two different biomolecules simultaneously in e.g. leaf cells.

In one aspect, the present disclosure pertains to method for introducing a biomolecule into an intact plant cell by a laser-assisted transfection method comprising the steps of:

(i) providing a plant explant isolated by any organ and tissue of a plant and comprising intact plant cells or an isolated plant cell and selectable marker;

(ii) providing a biomolecule and a selectable marker;

(iii) delivering said biomolecule and the selectable marker into the plant cell by a laser-assisted transfection method, wherein the cell or tissue is surrounded by a liquid and the laser focal point is in the liquid adjacent to the cell wall and not directly in contact with the cell wall.

The methods of the present disclosure may be applied to an intact differentiated cell like a plant cell. In particular, the cell may be comprised in a tissue and/or an organism. In some advantageous embodiments, the plant is a dicot or monocot, in particular plant species used in the methods provided herein belong to the Solanaceae family and is *Nicotiana benthamiana* or *N. tabacum*, although in a further aspect the plant species may be any monocot or dicot plant or algae, such as (without limitation) *Arabidopsis thaliana*; field crops (e.g., alfalfa, barley, bean, corn, cotton, flax, pea, rape, rice, rye, safflower, sorghum, soybean, sunflower, tobacco, and wheat); vegetable crops (e.g., asparagus, beet, broccoli, cabbage, carrot, cauliflower, celery, cucumber, eggplant, lettuce, onion, pepper, potato, pumpkin, radish, spinach, squash, taro, tomato, and zucchini); fruit and nut crops (e.g., almond, apple, apricot, banana, blackberry, blueberry, cacao, cherry, coconut, cranberry, date, fajoa, filbert, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber).

In some advantageous embodiments, the intact differentiated plant cell is isolated from plant leaves, flowers, roots or cotyledons before providing the biomolecule.

In some advantageous embodiments, the biomoelcule is co-delivered with one or more components, including but not limited to dNTP, ddNTP, non-natural base analogues, di-nucleotides, trinucleotides, oligonucleotides, enzyme inhibitors, sugars, amino acids, proteins, antibodies, transcription factors and other DNA-binding proteins, ribonucleic acids in the form of mRNA, siRNA, miRNA.

Based on these findings, the inventors developed a novel method for the generation of transformed plants through the transfection of intact plant cells with a biomolecule like an expression vector/expression cassette. For example, a high-powered multiphoton laser may be focused 2-5 µm below a leaf sample comprising intact plant cells and briefly irradiated the sample at a laser power of ~2 W. The laser power may be kept at 70%. In addition, the offset, Gain and EOM of the laser pulsing controller maybe kept at 0.00.

Pulsed operation of lasers refers to any laser not classified as continuous wave, so that the optical power appears in pulses of some duration at some repetition rate. Other laser like Nd:YAG laser was also used to create a pulse energy varied between 260 to 335 µJ. Continuous waves also can be used with a $\lambda=975$ nm, laser power of 0.7 kW/cm$^2$ (Padilla-Martinez et al., 2014). The mentioned laser-associated transfection method can be used for the direct delivery of RNPs into the intact cells of e.g. tobacco leaf discs, which are easy to prepare and handle, thus avoiding the laborious preparation of protoplasts or zygotes. A preassembled RNP comprising the Cas9 protein, crRNA and ATTO-550-labeled tracrRNA targeting the tobacco pds or actin depolymerizing factor (adf) genes is introduced in the leaf cells. The fluorescent tracrRNA allows the direct screening of transfected cells and makes the use of a selectable marker gene unnecessary. Nevertheless, RNP-mediated genome editing is generally laborious because the absence of a selectable marker gene still requires a time-consuming screening process in order to identify rare mutants in a large background of wild-type cells.

In some advantageous embodiments, the methods according to the present disclosure comprise the further step of identifying the cells transfected with the biomolecule by microscopy, in particular by fluorescence microscopy when using a fluorescent visual marker labeled to the biomolecule.

In another embodiment, the methods according to the present disclosure comprise further the step of selecting the cells transfected with the biomolecule and optionally regenerating the cells to intact plantlets by growing in and/or on a growth media. For example, the selected cells comprising the biomolecule can be used for the regeneration of cell lines, whole tissues or organisms.

Plant tissue and cell culture growth media according to the present disclosure are generally made up of some or all of the following components: macronutrients, micronutrients, vitamins, amino acids or other nitrogen supplements, sugar(s), other undefined organic supplements, solidifying agents or support systems, and growth regulators. Several media formulations are commonly used for the majority of all cell and tissue culture work, e.g. Banana Medium, BM Medium, CHU (N6) Medium, Gamborg B5 Medium, Linsmaier & Skoog Medium, Murashige & Skoog Medium (MS), Modified MS Medium, Nitsch Medium, Orchid Medium, Schenk & Hildebrandt Medium.

A further advantageous embodiment of the present disclosure pertains to a method of producing a transformed plant by introducing an expression vector into an intact plant cell with a laser-assisted transfection method comprising the steps of:

(i) providing an intact plant or a plant explant isolated by any organ and tissue of a plant and comprising intact plant cells;

(ii) providing an expression vector and a selectable marker;

(iii) layering the intact plant or the plant explant onto a formulation comprising an expression vector and a selectable marker in a transparent support;

(iv) delivering said expression vector and the selectable marker into a plant cell of the plant explant with laser-assisted transfection, wherein the cell is surrounded by a liquid and the laser focal point is in the liquid adjacent to the cell wall and not directly in contact with the cell wall;

(v) identifying the cells transfected with the expression vector;

(vi) selecting the cells transfected with the expression vector from the plant explant (vii) regenerating the cells to intact plantlets by growing in and/or on a growth media.

In some embodiments, the method comprises the further step of:

(viii) analyzing the plantlets to confirm the transfection of the target gene using any method for genetic characterization of transformed plants;

(ix) selecting the analyzed plantlets scoring positive and further growing those plantlets to full plants.

A further advantageous embodiment of the present disclosure pertains to a method for introducing a biomolecule into an intact plant cell by a laser-assisted transfection method comprising the steps of:

(i) providing an intact plant or a plant explant isolated by any organ and tissue of a plant and comprising intact plant cells;

(ii) providing a biomolecule and a selectable marker;

(iii) layering the intact plant or the plant explant onto a formulation comprising a biomolecule and a selectable marker in a transparent support;

(iv) delivering said biomolecule and the selectable marker into a plant cell of the plant or plant explant with laser-assisted transfection, wherein the cell is surrounded by a liquid and the laser focal point is in the liquid adjacent to the cell wall and not directly in contact with the cell wall;

(v) identifying the cells transfected with the biomolecule;

(vi) selecting the cells transfected with the biomolecule from the plant explant (vii) regenerating the cells to intact plantlets by growing in and/or on a growth media.

In some embodiments, the method comprises the further step of:

(viii) analyzing the plantlets to confirm the transfection of the biomolecule by using any method for genetic and/or proteome characterization of transformed plants;

(ix) selecting the analyzed plantlets scoring positive and further growing those plantlets to full plants.

A "transparent support" includes any support that can transmit light of different wavelength spanning the visible spectrum and beyond, i.e. in the UV range and/or in the near infrared, infrared and far-infrared spectrum. A transparent support includes but it is not limited to any glass support, any quartz support, any borosilicate support or any optical grade plastic support including but not limited to any polyethylene, polystyrene, cyclic olefin polymers and other polymers made supports of any thickness as known to those skilled in the art.

A "method for genetic characterization of a transformed plant" includes any method to obtain information on the DNA sequence of one or more gene(s) and/or allele(s) thereof, with the scope to confirm that the plant derived by the transformation method of the present invention has been successfully modified for the particular target gene or genes. For the methods according to the present disclosure the genetic characterization is carried out by using any technique known to those skilled in the art including but not limited to Sanger sequencing, any next generation sequencing approach including but not limited to pyrosequencing, SOLiD sequencing, sequencing by synthesis (SBS) or any other sequencing method knows to those skilled in the art or any other method suitable to derive information on the allelic composition of the transformed plant including but not limited to high resolution melt analysis (HRMA).

In some examples of the present description, an ATTO-550-labeled biomolecule allowed the rapid identification of transfected cells by fluorescence microscopy. The biomolecule-containing cells are screened 48 h after the laser-assisted transfection, identified and selected biomolecule-containing cells are excised at small leaf tissue fragments of different sizes (~0.1-0.3 cm radius) depending on the intensity and distribution of the biomolecule signal. The selected leaf fragments are grown on MS medium to regenerate intact plantlets. Following regeneration, a simple PCR-based HRMA procedure can be used to identify the mutants because this method has sufficient resolution to detect single-nucleotide changes [Hidalgo-Grass et al., 2010; Denbow et al., 2018; Li et al., 2018]. In this manner, it is possible to screen 96 plants in 2 h, a much higher throughput than it could be achieved using e.g. the T7 assay for detection and selection of mutants [EP3392339]. A total of 1673 plants in the pds gene editing experiment were analyzed and 147 homozygous or biallelic mutants and 442 heterozygous mutants were identified. The homozygous or biallelic mutants were characterized in more detail by Sanger sequencing across the target site, revealing 93 homozygous and 54 biallelic mutants and confirming the positive HRMA results.

In an advantageous embodiment, the present disclosure pertains also to a method for introducing a biomolecule into an intact plant cell by a laser-assisted transfection method comprising the steps of:

(i) providing a plant explant isolated by any organ and tissue of a plant and comprising intact plant cells;

(ii) providing a biomolecule and a selectable marker;

(iii) delivering said biomolecule into the plant cell by a laser-assisted transfection method, wherein the cell or tissue is surrounded by a liquid and the laser focal point is in the liquid adjacent to the cell wall and not directly in contact with the cell wall.

In some advantageous embodiments, the intact cell(s) is obtained from a non-sterile environment and/or provided under a non-sterile environment, e.g. a plant that is grown in a green house, a growth chamber, a field, a habitat, or a natural environment.

In some advantageous embodiments the intact cell(s) are further cultivated in a non-sterile environment after the biomolecule has been delivered to said intact cells(s). Such non-sterile environments may e.g. comprise a laboratory, a room, a green house, a growth chamber, a growth cabinet, a field, a garden, or a natural environment.

In some advantageous embodiments, the intact differentiated cell(s) are exposed to stress condition before and/or while delivering the biomolecule, including but not limited to UV-stress, heat-stress, cold-stress, draught, reactive oxygen-species or chemicals.

In particular, the genome-modifying formulation, in particular the biomolecule comprise a selectable marker. A marker is a detectable genetic trait or segment of DNA that can be identified and tracked. A marker gene typically serves as a flag for another gene, sometimes called the target gene. A marker gene is typically used with a target gene being used to transform target cells. Target cells that heritably receive the target gene can be identified by selecting for cells that also express the marker gene. The marker gene is near enough to the target gene so that the two genes (the marker gene and the target gene) are genetically linked and are usually inherited together.

In some further embodiments, the laser is a multiphoton laser operating under pulsing conditions and wherein the laser power is between 0.5 W and 3 W, preferably about 2 W, more preferably wherein the laser power is between 65 and 90%, preferably at 70% of 2 W and wherein preferably the wavelength is between 700 nm and 900 nm, preferably 800 nm.

METHODS AND EXAMPLES

In the following examples, materials and methods of the present disclosure are provided. It should be understood that these examples are for illustrative purpose only and are not to be construed as limiting this disclosure in any manner. All publications, patents, and patent applications cited herein are hereby incorporated by reference in their entirety for all purposes.

Example 1: Laser-Assisted Transfection Introduction of DsRed Protein as a Biomolecule into *N. tabacum* Leaves To test the delivery of proteins into cells through laser-assisted transfection method recombinant DsRed protein was used (Discosoma sp.red fluorescent protein gene; R2G mutant; Sack et al., 2015) for the initial experiments. In order to standardize the transfection conditions, wild-type tobacco plants (3-4 months old, when the plants had reached the 4-6 leaf stage) were used. The leaf discs (~10×5 mm) were placed in a microscopy-grade 35-mm petri dish with a glass bottom (ibidi μ-dish) containing 20 μL 0.25 μg/μL DsRed. The mid-rib was removed and the remaining leaf area was cut into approximately 10 mm×5 mm size (FIG. 1B). After several irradiation tests with the laser we identified conditions that promoted a local transient increase in membrane permeability without affecting cell viability. For all experiments, with our confocal system this was achieved by setting the laser power between 0.5 and 3 W more preferably to ~2 W and by tuning the laser at a wavelength between 700 and 1200 nm more preferably at a wavelength of 800 nm. Moreover, by using the controller integrated in the software of the confocal system we further adjusted the laser power between at least 65 and 90% and more preferably at 70% of the nominal power of 2 W indicated above. In addition, the offset, gain and electro-optical modulator (EOM) settings of the laser controlling mask of the microscope software were both set to 0.00. The laser focal point was focused at 2-5 μm below the leaf sample and the plant tissue was irradiated by a short laser pulse focused to a very restricted region of the leaf sample targeting an area of approx. 2-3 cells. For this purpose we used a 40× water immersion objective. However, objectives of lower or higher magnification (e.g. a 20× or a 60× objectives) with dry or immersion lenses are also suitable for laser irradiation after fine-tuning the power settings. The resulting used laser-assisted transfection method transiently increased the permeability of the plasma membrane, allowing the uptake of DsRed into the leaf cells.

Example 2: Identification of DsRed Protein by Fluorescence Microscopy

Figure 2:
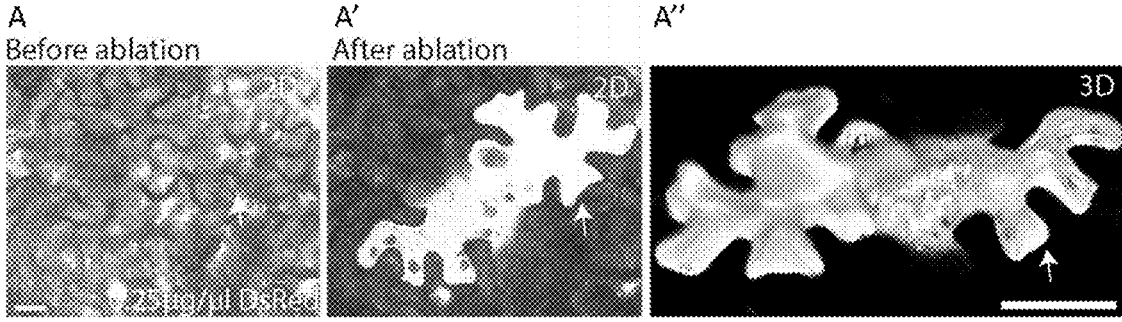
FIG. 2: A) Tobacco leaves before the laser-assisted treatment. The white arrow points to the region chosen for laser targeting. Scale bar=50 μm. A') The same region after the laser-assisted uptake of 20 μL DsRed solution (0.25 μg/μL). DsRed fluorescence was detected by confocal microscopy. A") 3D reconstruction of DsRed-positive cells after laser treatment. Scale bar=50 μm.

To confirm penetration of DsRed in individual cells leaf explant cells were analyzed before and after the laser pulse by confocal microscopy (FIGS. 2A and A'). A 3D-reconstruction of the transfected cells confirmed that DsRed was homogenously distributed in the cytoplasm (FIG. 2A") and not merely distributed on the tissue surface. The introduction of DsRed protein into the leaves using the laser-assisted transfection method according to the present disclosure was also confirmed by visually inspecting the leaf discs under an Olympus X71 inverted fluorescence microscope using a fluorescence filter with an excitation peak of approximately 558 nm and an emission peak of approximately 583 nm for the detection of DsRed fluorescence.

Figure 3:
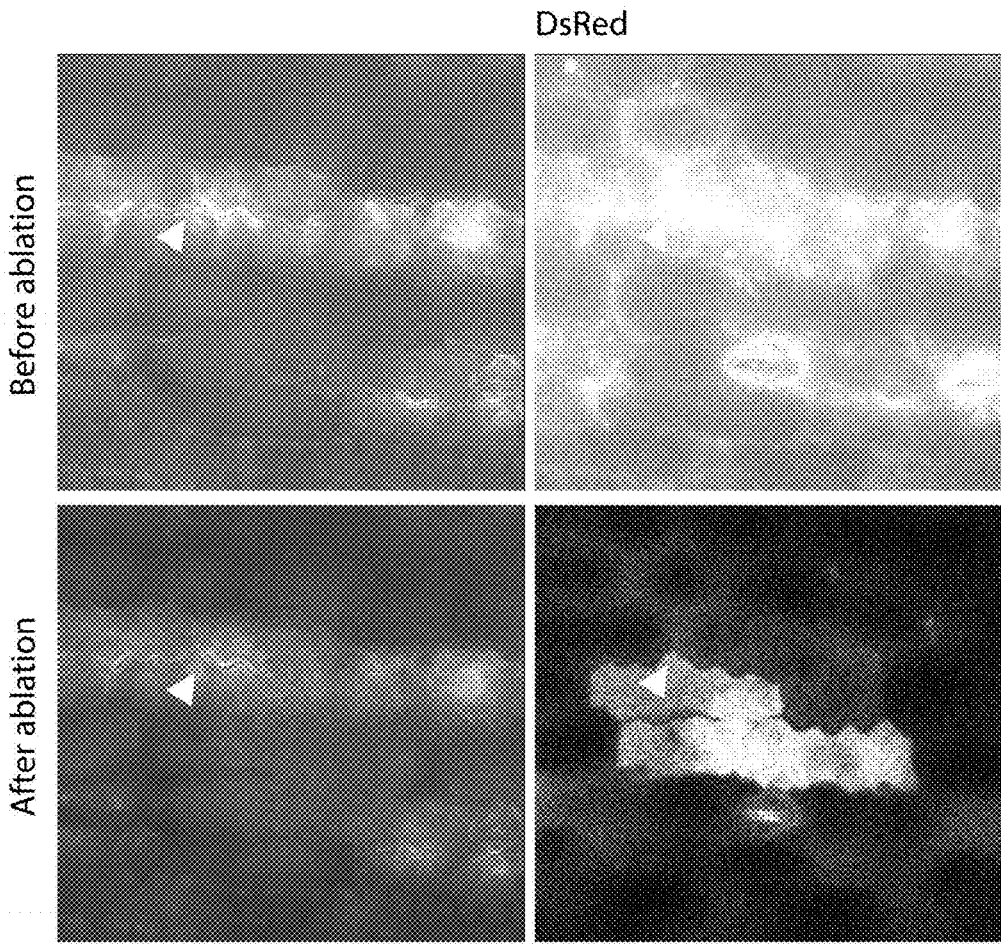
FIG. 3: Zea mays leaves before and after the laser-assisted transfection. White arrows point to the region chosen for laser targeting. Scale bar=50 μm.

Example 3: Laser-Assisted Transfection Method Introduction of DsRed Protein into *Z. mays* Leaves To further confirm the delivery of proteins into cells through the laser-assisted transfection method according to the present disclosure, the inventors used recombinant DsRed protein and explants obtained from 1-month-old *Z. mays* leaves, a monocotyledon crops. The experiment set up was as like example 1 and after the introduction of DsRed protein into the cells we identified the fluorescence as like example 2 (FIG. 3).

Example 4: Designing of crRNA

Genomic DNA was extracted from wild-type tobacco plants (3-4 months old, when the plants had reached the 4-6 leaf stage) [Pospíšilová et al., 1998] using the NucleoSpin Plant II kit (Macherey & Nagel). The target regions of the selected pds and adf genes were amplified from genomic DNA using a high-fidelity PCR system (Q5 high-fidelity DNA polymerase). The PCR products were purified from agarose gels using the NucleoSpin gel and PCR clean-up kit (Macherey & Nagel) and sequenced using the Sanger method prior to gRNA design, using the primers listed in the table 1. The gRNA sequences were designed using the Crispr RGEN Tools, Cas-Designer and CRISPR-P v2.0 online. The gRNA targeting the pds gene was 5'-TTT TTT TGG AAT ATC AGG TTT GG-3' (SEQ ID NO:1) and the gRNA targeting the adf gene was 5'-CTT GGA GCT GAA GAG GAA GAA GG-3' (SEQ ID NO:2). BLAST analysis was used to identify any potential off-targets in the crRNA sequences.

TABLE 1

| Gene | Primer sequence |
|------|-----------------|
| adf | 5'-ATGTCTTTCAGATTCAGAGGG-3' (SEQ ID NO: 3) 5'-TCAGTGAGCGCGGTCTTT-3' (SEQ ID NO: 4) |
| pds | 5'-CTTGATTTTGTGGGTGAAGGA-3' (SEQ ID NO: 5) 5'-GCAAGGCAGAATACAGATCG-3' (SEQ ID NO: 6) |

Example 5: Preparation of RNP Complex

To prepare RNP complexes, we used crRNA, tracrRNA labeled with ATTO-550 and Cas9 protein synthesized by Integrated DNA Technologies, Inc. (IDT). We used crRNA-XT for all experiments, which has additional chemical modifications to optimize stability and performance. We mixed the crRNA and tracrRNA in equimolar concentrations. For all the experiments we used 100 μM concentration of crRNA and ATTO 550 labelled tracrRNA. For preparation of the RNP complex we initially heated the crRNA and ATTO 550 labelled tracrRNA 100 μM each at 95° C. for 5 minutes. Further 120 pmol from the gRNA mix, 104 pmol Cas9 protein and 2.1 μl of PBS were added to make a final volume of 5 μL of RNP complex and kept at room temperature for 20 minutes.

Figure 4:
FIG. 4: A) Detection of ATTO-550-labeled fluorescent RNPs in cells after laser-assisted transfection. Wild-type plants do not show any fluorescence. Scale bar=50 μm. B) Representative sampling of RNP-containing regions of different sizes (~0.1-0.3 cm in radius) depending on the intensity of the RNP signal. Scale bar=1 cm.

Example 6: Targeting Endogenous pds Gene Through Delivery of RNP Complex into *N. tabacum* Intact Leaf Cells Using the Laser-Assisted Transfection The crRNA was designed as like example 4 and the RNP complex was prepared as like example 5. Immediately after the preparation of RNP complex it was introduced into 3-4 months old *N. tabacum* intact leaf discs, which are easy to prepare and handle, thus avoiding the laborious preparation of protoplasts or zygotes. After the introduction of RNP the leaves were kept on MS medium (4.4 g/L MS-salts with vitamins (Duchefa M0222), 20 g/L sucrose, 0.6 mg/L thiamine-HCl, 7 g/L agar, pH 5.8) for 48 h. The leaf discs were visually inspected under an Olympus X71 inverted fluorescence microscope with an excitation peak of approximately 558 nm and an emission peak of approximately 583 nm for the detection of ATTO 550, 48 h post-transfection (FIG. 4A). Regions showing fluorescence were excised using pipette tips (1 mL and 200 μL capacity, shortened with scissors to achieve a radius of 0.1-0.3 cm) according to the area of RNP fluorescence (FIG. 4B). The selected regions containing the pds RNPs were transferred to MS medium (4.4 g/L MS-salts with vitamins (Duchefa M0222), 20 g/L sucrose, 0.6 mg/L thiamine-HCl, 7 g/L agar, pH 5.8) with hormones (1 mg/L 6-BAP, 0.1 mg/L NAA) and kept at 20-230° C. The regenerated tissue was subcultured onto plates with fresh medium every 2 weeks until shoots appeared. All plants were regenerated without selection reagents such as antibiotics.

Example 7: Targeting Endogenous adf Gene Through Delivery of RNP Complex into *N. tabacum* Intact Leaf Cells Using the Laser-Assisted Transfection Method The crRNA was designed as like example 4 and the RNP complex was prepared as like example 5. The endogenous adf gene was targeted as like example 5 using the corresponding gRNA. After the introduction of RNP, the tissue was allowed to regenerate onto plates with fresh medium, which was described in example 6 every 2 weeks until shoots appeared. The plantlets were then transferred onto MS medium without hormones and incubated at 20-25° C. with a 16-h photoperiod (7000 lux) to induce root formation. Adf plants with roots were transferred to ED73 standard soil (Patzer) with 0-30% (v/v) sand, and grown in the greenhouse with a 16-h photoperiod (10000 lux, plus sunlight) at 70-90% humidity. All plants were regenerated without selection reagents such as antibiotics.

Example 8: Analysis of pds Gene Phenotype

Figure 5:
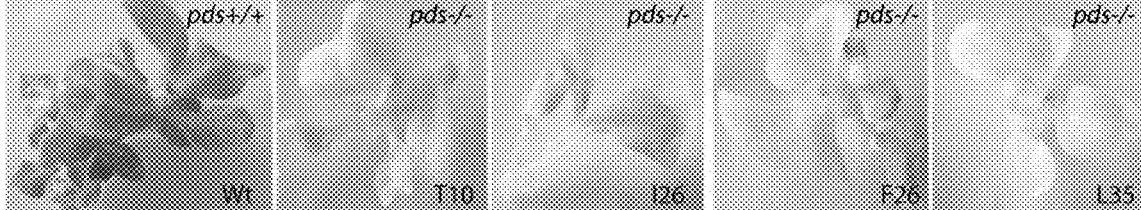
FIG. 5: Albino pds −/− homozygous mutant lines T10, 126, F26 and L35 generated with the method of the present invention and compared to a wild-type plant.

After the regeneration of the shoots, the inventors visually identified the albino phenotypes resulting for homozygous mutation of pds gene. Representative images of homozygous pds mutant plants with the anticipated albino phenotypes (homozygous lines F19, T10, L35 and 126) are provided in FIG. 5. By selecting the region containing the cells transfected with RNPs, the inventors were able to avoid the inclusion of large numbers of wild-type cells to facilitate the screening and regeneration of mutants.

Example 9: Analysis of pds Gene Mutation Using High Resolution Melt Analysis (HRMA) and Confirmation Using Sanger Sequencing Following regeneration, the inventors used a simple PCR-based HRMA procedure to identify the mutants because this method has sufficient resolution to detect single-nucleotide changes [Hidalgo-Grass C and Strahilevitz J, 2010; Denbow et al., 2018; Li et al., 2018]. HRMA is also simpler, more sensitive, more specific, less expensive and quicker than other screening methods [Hung et al., 2008; Kennerson et al., 2007; McKinney et al. 2004; Willmore et al., 2004; Zhou et al., 2004]. In this manner, the inventors were able to screen 96 plants in 2 h, a much higher throughput than previously achieved using the T7 assay for detection and selection of mutants [Bortesi et al., 2017]. A total of 1673 plants were analyzed in the pds gene editing experiment and identified 147 homozygous/biallelic mutants and 442 heterozygous mutants. The melting curve of pds homozygous mutant T10 is compared to the wild-type control in FIG. 6A. The primers used for HRMA is given in table 2. The homozygous/biallelic mutants were characterized in more detail by Sanger sequencing across the target site, revealing 93 homozygous and 54 biallelic mutants and confirming the positive HRMA results (FIG. 6B). The Sanger sequencing primers are given in table 2. A representative chromatogram peak analysis is provided for line T10 in FIG. 6C, showing a large deletion upstream of the PAM signal. With the laser-assisted transfection method according to the present disclosure, the inventors achieved an overall mutation efficiency of 8.7% in the pds gene within a very short time period (approximately 7-8 months).

TABLE 2

| Gene | Primer sequence |
|---|---|
| pds HRM | 5'-ATCTGGCTGATGCTGGTCAC-3' (SEQ ID NO: 7) 5'-AAGGAATAAAATTAAAGGAAAGCATG-3' (SEQ ID NO: 8) |
| pds Seq | 5'-CCATTGACCGGTTAGCAGTT-3' (SEQ ID NO: 9) 5'-TGAACACCCTTGCAATTGTTTGAG-3' (SEQ ID NO: 10) |

Figure 7:
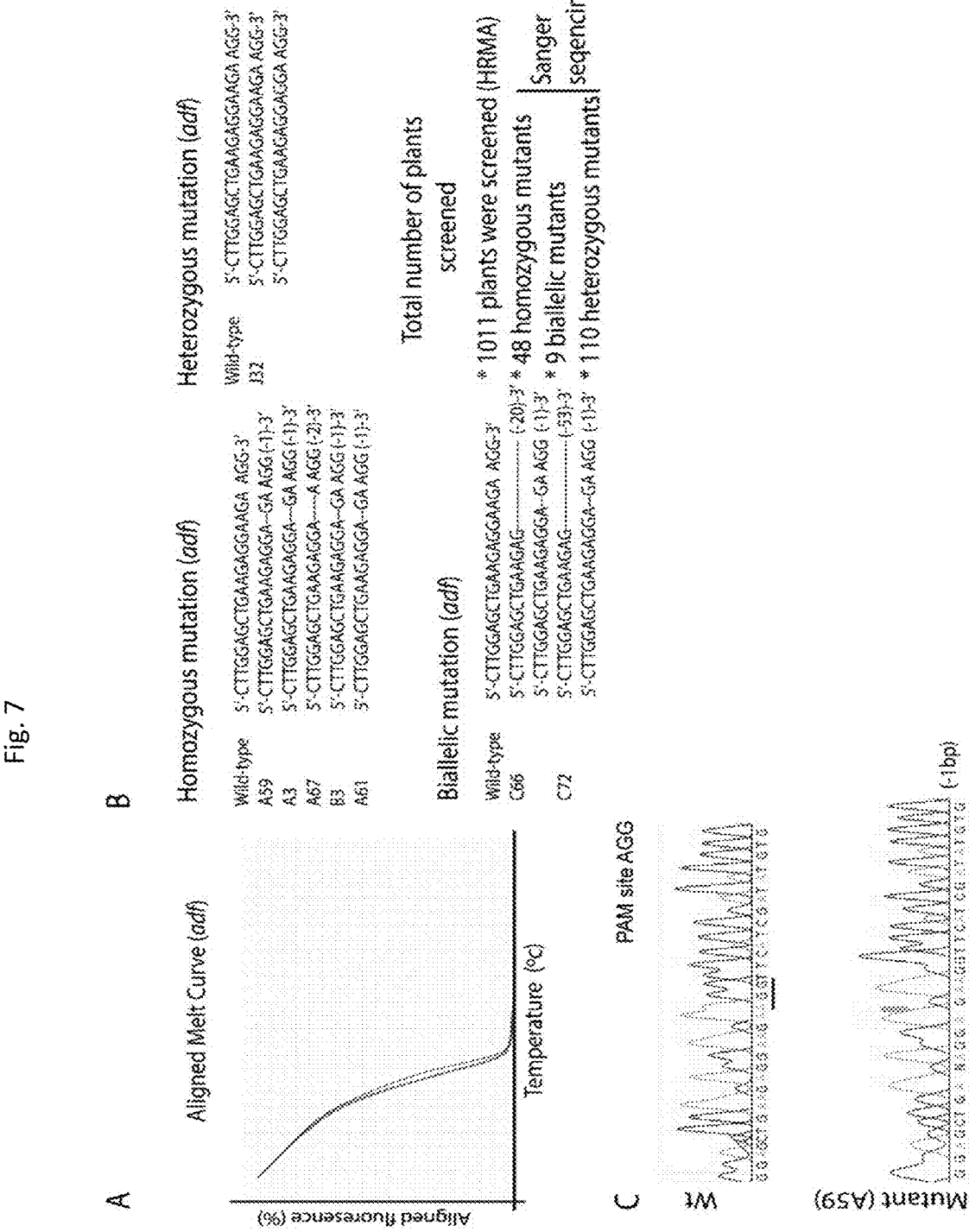
FIG. 7: A) Representative image showing the high-resolution melt analysis of an adf mutant (line A59) generated and selected with the method of the present invention. B) Sequence alignment of genome-edited mutants. C) Exemplary chromatogram analysis of wild-type (wt) and mutant plant (line A59).

Example 10: Analysis of adf Gene Mutation Using High Resolution Melt Analysis and Confirmation Using Sanger Sequencing 1011 plants were analyzed by HRMA in the adf gene editing experiment and identified 57 homozygous/biallelic mutants and 110 heterozygous mutants. The primer sequences used for HRMA are given in table 3. In the former group, Sanger sequencing confirmed the positive HRMA results and resolved 48 homozygous mutants and 9 biallelic mutants. The Sanger sequencing primers are given in table 3. The melting curve of adf homozygous mutant A59 is compared to the wild-type control in FIG. 7A. Representative results for the homozygous, biallelic and heterozygous mutants are provided in FIG. 7B. Sanger sequencing specified the nature of the mutations (a representative chromatogram for homozygous mutant A59 is provided in FIG. 7C and shows a single-base deletion at the PAM site).

TABLE 3

| Gene | Primer sequence |
|---|---|
| adf HRM | 5'-TTCTGGCATGGGTGTAGCTG-3' (SEQ ID NO: 11) 5'-adf-3' |
| adf Seq | 5'-AGTCAAGGTGCCTGCAATTTA-3' (SEQ ID NO: 13) 5'-CAAAGAAAATCTTGCTCTTTGG-3' (SEQ ID NO: 14) |

Example 11: Further Analysis of the adf Mutants

Figure 8:
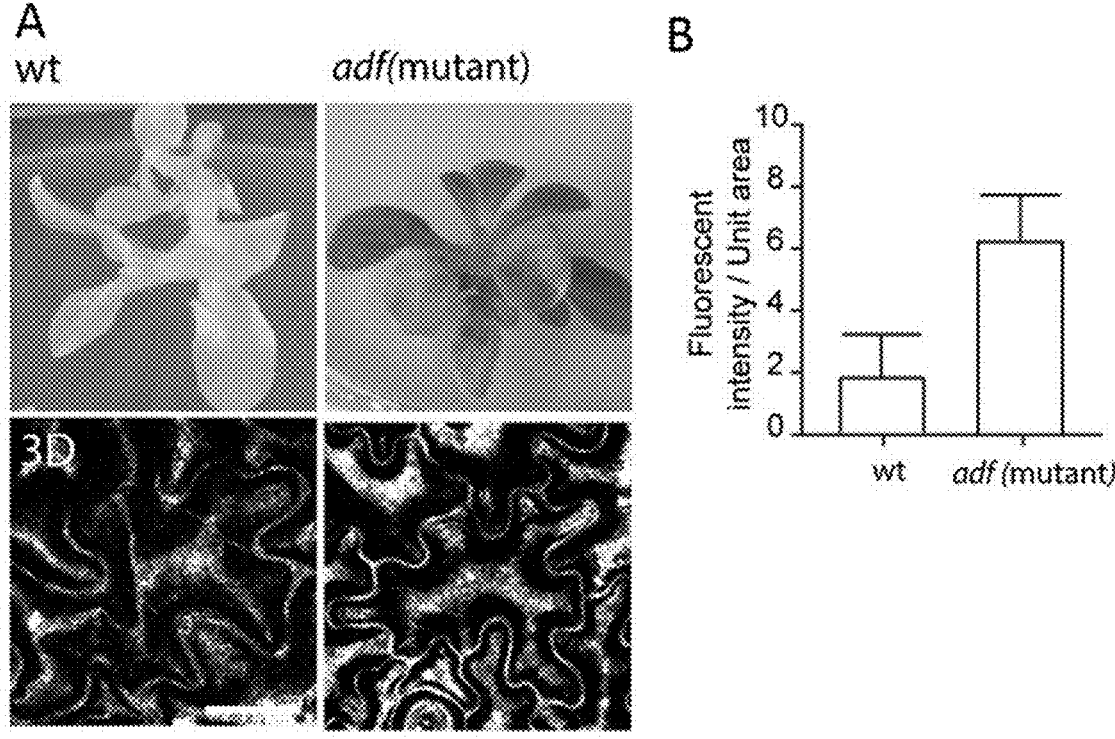
FIG. 8: A) Representative image of wt and adf mutant plants of the present invention with corresponding phalloidin stained cells. Scale bar=50 μm. B) Image analysis of average actin intensity normalized by the area of fluorescence in wt and adf mutant (line A59) cells using ImageJ.

For further confirmation, the inventors stained T0 adf mutant plants with phalloidin to visualize the anticipated enhanced formation of actin filaments [Augustine et al., 2015]. The principal components of the actin cytoskeleton include monomeric actin (G-actin) and filamentous actin (F-actin), with G-actin being the dominant form [Nan et al., 2017; Hugo et al., 2017]. The role of adf is to depolymerize F-actin to G-actin. Thus, a mutation in the adf gene should promote the formation of more F-actin. Accordingly, confocal microscopy confirmed the presence of more actin filaments in the leaves of T0 adf mutant plants compared to wild-type plants (FIG. 8A) based on image analysis of the actin fluorescence intensity normalized by the area of the stained actin using ImageJ (FIG. 8B). Representative images of the wild-type and adf mutant plantlets (line A59) 2-3 months after transfection with RNP (FIG. 8A) and of adult mutant T0 plants grown in the greenhouse showed that the adf mutation did not have a significant effect on the morphological phenotype.

REFERENCES

Augustine S M, Cherian A V, Syamaladevei D P and Subramonian N (2015) Erianthus arundinaceus HSP70 (EaHSP70) acts as a key regulator in the formation of anisotropic interdigitation in sugarcane (Saccharum spp. hybrid) in response to drought stress. Plant and Cell Physiology 56:2368-80.

Bortesi, L., Augustine, S. M., Fischer, R., Sack, M., and Zischewski, J. (2017). EU3392339. Improved genome editing in plant cells. (Patent application no. EP 17166753.8.).

Denbow, C., Ehivet, S. C. and Okumoto, S. (2018). High Resolution Melting Temperature Analysis to Identify CRISPR/Cas9 Mutants from *Arabidopsis*. Bio Protoc 8(14): e2944.

Hidalgo-Grass C and Strahilevitz J (2010) High-Resolution Melt Curve Analysis for Identification of Single Nucleotide Mutations in the Quinolone Resistance Gene aac(6')-Ib-crV. Antimicrobial Agents and Chemotherapy. 54(8): 3509-3511.

Hugo Wioland, Berengere Guichard, Yosuke Senju, Sarah Myram, Pekka Lappalainen, Antoine Jegou, Guillaume Romet-Lemonne. ADF/Cofilin accelerates actin dynamics by severing filaments and promoting their depolymerization at both ends. Current Biology 27, 1956-1967. Jul. 10, 2017.

Hung, C., Lee, C., Chang, C., Jong, Y., Chen, C., Hseih, W., Su, Y. and Lin, W. (2008) Genotyping of the G1138A mutation of the FGFR3 gene in patients with achondroplasia using high-resolution melting analysis. Clin. Biochem. 41: 162-166.

Kennerson, M., Warburton, T., Nelis, E., Brewer, M., Polly, P., De Jonghe, P., Timmerman, V. and Nicholson, G. (2007) Mutation scanning the GJB1 gene with high-resolution melting analysis: implications for mutation scanning of genes for Charcot-Marie-Tooth disease. Clin. Chem. 53, 349-352.

Li, S., Liu, S., Liu, Y., Lu, H., Tan, Y., Huang, J., Wei, P., and Shu, Q. Y. (2018). HRM-facilitated rapid identification and genotyping of mutations induced by CRISPR/Cas9 mutagenesis in rice. Crop Breed. Appl. Biotechnol. 18(2): 184-191.

Martin-Ortigosa, S. and Wang, K. (2014). Proteolistics: a biolistic method for intracellular delivery of proteins. Transgenic Res. 23(5):743-756.

McKinney, J., Longo, N., Hahn, S., Matern, D., Rinaldo, P., Strauss, A. and Dobrowolski, S. (2004) Rapid, comprehensive screening of the human medium chain acyl-CoA dehydrogenase gene. Mol. Genet. Metab. 82, 112-120.

Nan Q, Dong Qian, Yue Niu, Yongxing He, Shaofei Tong, Zhimin Niu, Jianchao Ma, Yang Yang, Lizhe An, Dongshi Wan, Yun Xiang (2017) Plant Actin-Depolymerizing Factors possess opposing biochemical properties arising from key amino acid changes throughout evolution. The Plant Cell, 29: 395-408.

Padilla-Martinez J P, Berrospe-Rodriguez C, Aguilar G, Ramirez-San-Juan J C and Ramos-Garcia R (2014). Optic cavitation with CW lasers: A review. Physics of Fluids 26, 122007.

Pospíšilová, J., Wilhelmová, N., Synková, H., Čatský, J., Krebs, D., Tichá, I., Hanáčková, B., Snopek, J. (1998). Acclimation of tobacco plantlets to ex vitro conditions as affected by application of abscisic acid. -J. exp. Bot. 49: 863-869.

Sack M, Rademacher T, Spiegel H, Boes A, Hellwig S, Drossard J, Stoger E and Fischer R (2015). From gene to harvest: insights into upstream process development for the GMP production of a monoclonal antibody in transgenic tobacco plants. Plant Biotechnology Journal 13:1094-105.

Willmore, C., Holden, J., Zhou, L., Tripp, S., Wittwer, C. and Layfield, L. (2004) Detection of c-kit-activating mutations in gastrointestinal stromal tumors by high-resolution amplicon melting analysis. Am. J. Clin. Pathol. 122, 206-216.

Zhou, L., Vandersteen, J., Wang, L., Fuller, T., Taylor, M., Palais., B. and Wittwer, C. (2004) High-resolution DNA melting curve analysis to establish HLA genotypic identity. Tissue Antigens 64, 156-164.

What is claimed is:

1. A method of producing a transformed plant by introducing an expression vector into an intact plant cell with a laser-assisted transfection method comprising the steps of:
   (i) providing an intact plant or a plant explant isolated from any organ and or tissue of a plant and comprising intact plant cells or an isolated plant cell with a cell wall;
   (ii) providing an expression vector and a selectable marker;
   (iii) delivering said expression vector and the selectable marker into the plant cell by a laser-assisted transfection method, wherein the cell or tissue is surrounded by a liquid, and the laser focal point is within the liquid adjacent to the cell with a cell wall and not directly on the cell with a cell wall;
   (iv) identifying the cells transfected with the expression vector; and
   (v) selecting the cells transfected with the expression vector and regenerating the cells to intact plantlets by growing in and/or on a growth media.

2. The method according to claim 1, further comprising the step of screening the transformed plants, optionally by genetic characterization.

3. The method according to claim 1, wherein the selectable marker is a visual marker, a gene encoding a visual marker, a gene that confers resistance to antibiotic or any other marker that can be used to select and/or identify transformed plants and/or plant tissue or is a combination of more than one selectable markers, and wherein the cells transfected with the expression vector and the selectable marker are identified by microscopy and/or by cultivation on solid medium containing appropriate selective agents.

4. The method according to claim 1, wherein the expression vector comprises a gene of interest and a selectable marker gene, and wherein the expression vector is delivered into the plant cell in combination with a separate visual marker molecule.

5. The method according to claim 1, wherein the laser irradiation conditions are adjusted for delivering of the expression vector by the laser-assisted transfection method with a cell membrane impermeable fluorescent substance, which is not passively or actively taken up by the intact plant cell.

6. A method for introducing a biomolecule into an intact plant cell by a laser-assisted transfection method comprising the steps of:
   (i) providing a plant explant isolated from any organ and or tissue of a plant and comprising intact plant cells or an isolated plant cell with a cell wall and a selectable marker;
   (ii) providing a biomolecule and a selectable marker; and
   (iii) delivering said biomolecule and the selectable marker into the plant cell by a laser-assisted transfection method, wherein the cell or tissue is surrounded by a liquid and the laser focal point is within the liquid adjacent to the cell with a cell wall and not directly on the cell with a cell wall.

7. The method according to claim 6, wherein the biomolecule is selected from the group consisting of DNA, RNA, a polypeptide, a protein and a combination thereof.

8. The method according to claim 6, wherein the method further comprises the step of screening of the transfected plant cells, optionally by genetic characterization.

9. The method according to claim 6, wherein the selectable marker is a visual marker, a gene encoding a visual marker, a gene that confers resistance to antibiotic or any other marker that can be used to select and/or identify transformed plants and/or plant tissue or is a combination of selectable markers, and wherein the cells are transfected with an expression vector and the selectable marker is identified by microscopy, and/or by cultivation on solid medium containing appropriate selective agents.

10. The method according to claim 9, wherein the expression vector comprises a gene of interest and a selectable marker gene, and wherein the expression vector is delivered into the plant cell in addition with a separate visual marker molecule.

11. The method according to claim 6, wherein the method further comprises the step of selecting the cells transfected with the biomolecule and optionally regenerating the cells to intact plantlets by growing in and/or on a growth media.

12. The method according to claim 6, wherein a plurality of different biomolecules are introduced into an intact plant.

13. The method according to claim 6, wherein the laser irradiation conditions are adjusted for delivering the biomolecule by the laser-assisted transfection method.

14. The method according to claim 1, wherein the laser is a multiphoton laser operating under pulsing conditions and wherein the laser power is between 0.5 watts and 3 watts and the wavelength is between 700 nm and 900 nm.

15. The method according to claim 1, wherein said plant is selected from the group consisting of bean, pea, soybean, sunflower, cereal species including maize, rice, wheat and trees including Gymnosperms and hardwood.

16. The method according to claim 3, wherein the microscopy is fluorescence microscopy.

17. The method according to claim 9, wherein the microscopy is fluorescence microscopy.

\* \* \* \* \*

SEQUENCE LISTING

<160> NUMBER OF SEQ ID NOS: 46

<210> SEQ ID NO 1
<211> LENGTH: 23
<212> TYPE: DNA
<213> ORGANISM: Nicotiana tabacum

<400> SEQUENCE: 1 ttttttttgga atatcaggtt tgg                                                    23

<210> SEQ ID NO 2
<211> LENGTH: 23
<212> TYPE: DNA
<213> ORGANISM: Nicotiana tabacum

<400> SEQUENCE: 2
cttggagctg aagaggaaga agg                                                     23

<210> SEQ ID NO 3
<211> LENGTH: 21
<212> TYPE: DNA
<213> ORGANISM: Artificial Sequence
<220> FEATURE:
<223> OTHER INFORMATION: adf gene primer sequence 1

<400> SEQUENCE: 3
atgtctttca gattcagagg g                                                       21

<210> SEQ ID NO 4
<211> LENGTH: 18
<212> TYPE: DNA
<213> ORGANISM: Artificial Sequence
<220> FEATURE:
<223> OTHER INFORMATION: adf gene primer sequence 2

<400> SEQUENCE: 4
tcagtgagcg cggtcttt                                                           18

<210> SEQ ID NO 5
<211> LENGTH: 21
<212> TYPE: DNA
<213> ORGANISM: Artificial Sequence
<220> FEATURE:
<223> OTHER INFORMATION: pds gene primer sequence 1

<400> SEQUENCE: 5
cttgattttg tgggtgaagg a                                                       21

```
<210> SEQ ID NO 6
<211> LENGTH: 20
<212> TYPE: DNA
<213> ORGANISM: Artificial Sequence
<220> FEATURE:
<223> OTHER INFORMATION: pds gene primer sequence 2

<400> SEQUENCE: 6
gcaaggcaga atacagatcg                                        20

<210> SEQ ID NO 7
<211> LENGTH: 20
<212> TYPE: DNA
<213> ORGANISM: Artificial Sequence
<220> FEATURE:
<223> OTHER INFORMATION: pds HRM

<400> SEQUENCE: 7
atctggctga tgctggtcac                                        20

<210> SEQ ID NO 8
<211> LENGTH: 26
<212> TYPE: DNA
<213> ORGANISM: Artificial Sequence
<220> FEATURE:
<223> OTHER INFORMATION: pds HRM 2 primer

<400> SEQUENCE: 8
aaggaataaa attaaaggaa agcatg                                 26

<210> SEQ ID NO 9
<211> LENGTH: 20
<212> TYPE: DNA
<213> ORGANISM: Artificial Sequence
<220> FEATURE:
<223> OTHER INFORMATION: pds SEQ primer sequence 1

<400> SEQUENCE: 9
ccattgaccg gttagcagtt                                        20

<210> SEQ ID NO 10
<211> LENGTH: 24
<212> TYPE: DNA
<213> ORGANISM: Artificial Sequence
<220> FEATURE:
<223> OTHER INFORMATION: pds SEQ primer sequence 1

<400> SEQUENCE: 10
tgaacaccct tgcaattgtt tgag                                   24

<210> SEQ ID NO 11
<211> LENGTH: 20
<212> TYPE: DNA
<213> ORGANISM: Artificial Sequence
<220> FEATURE:
<223> OTHER INFORMATION: adf HRM primer sequence 1

<400> SEQUENCE: 11
ttctggcatg ggtgtagctg                                        20

<210> SEQ ID NO 12
<211> LENGTH: 20
<212> TYPE: DNA
<213> ORGANISM: Artificial Sequence
<220> FEATURE:
<223> OTHER INFORMATION: adf HRM primer sequence 1
```

-continued

```
<400> SEQUENCE: 12
gctgccagtt ttctcaacaa                                              20

<210> SEQ ID NO 13
<211> LENGTH: 21
<212> TYPE: DNA
<213> ORGANISM: Artificial Sequence
<220> FEATURE:
<223> OTHER INFORMATION: adf SEQ primer sequence 1

<400> SEQUENCE: 13
agtcaaggtg cctgcaattt a                                            21

<210> SEQ ID NO 14
<211> LENGTH: 23
<212> TYPE: DNA
<213> ORGANISM: Artificial Sequence
<220> FEATURE:
<223> OTHER INFORMATION: adf SEQ primer sequence 2

<400> SEQUENCE: 14
caaagaaaat cttgctcttt tgg                                          23

<210> SEQ ID NO 15
<211> LENGTH: 23
<212> TYPE: DNA
<213> ORGANISM: Nicotiana tabacum

<400> SEQUENCE: 15 ttttttgga atatcaggtt tgg                                           23

<210> SEQ ID NO 16
<211> LENGTH: 23
<212> TYPE: DNA
<213> ORGANISM: Nicotiana tabacum

<400> SEQUENCE: 16 ttttttgga atatcaggtt tgg                                           23

<210> SEQ ID NO 17
<211> LENGTH: 23
<212> TYPE: DNA
<213> ORGANISM: Nicotiana tabacum

<400> SEQUENCE: 17 ttttttgga atatcaggtt tgg                                           23

<210> SEQ ID NO 18
<211> LENGTH: 23
<212> TYPE: DNA
<213> ORGANISM: Nicotiana tabacum

<400> SEQUENCE: 18 ttttttgga atatcaggtt tgg                                           23

<210> SEQ ID NO 19
<211> LENGTH: 23
<212> TYPE: DNA
<213> ORGANISM: Nicotiana tabacum

<400> SEQUENCE: 19 ttttttgga atatcaggtt tgg                                           23
```

-continued

```
<210> SEQ ID NO 20
<211> LENGTH: 23
<212> TYPE: DNA
<213> ORGANISM: Nicotiana tabacum

<400> SEQUENCE: 20
tttttttgga atatcaggtt tgg                                                        23

<210> SEQ ID NO 21
<211> LENGTH: 23
<212> TYPE: DNA
<213> ORGANISM: Nicotiana tabacum

<400> SEQUENCE: 21
tttttttgga atatcaggtt tgg                                                        23

<210> SEQ ID NO 22
<211> LENGTH: 23
<212> TYPE: DNA
<213> ORGANISM: Nicotiana tabacum

<400> SEQUENCE: 22
tttttttgga atatcaggtt tgg                                                        23

<210> SEQ ID NO 23
<211> LENGTH: 10
<212> TYPE: DNA
<213> ORGANISM: Nicotiana tabacum

<400> SEQUENCE: 23
ttttttttgg                                                                       10

<210> SEQ ID NO 24
<211> LENGTH: 10
<212> TYPE: DNA
<213> ORGANISM: Nicotiana tabacum

<400> SEQUENCE: 24
ttttttttgg                                                                       10

<210> SEQ ID NO 25
<211> LENGTH: 18
<212> TYPE: DNA
<213> ORGANISM: Nicotiana tabacum

<400> SEQUENCE: 25
tttttttgga atatcagg                                                              18

<210> SEQ ID NO 26
<211> LENGTH: 17
<212> TYPE: DNA
<213> ORGANISM: Nicotiana tabacum

<400> SEQUENCE: 26
tttttttgga atatcag                                                               17

<210> SEQ ID NO 27
<211> LENGTH: 23
<212> TYPE: DNA
<213> ORGANISM: Nicotiana tabacum

<400> SEQUENCE: 27
tttttttgga atatcatgtt tgg                                                        23
```

```
<210> SEQ ID NO 28
<211> LENGTH: 23
<212> TYPE: DNA
<213> ORGANISM: Nicotiana tabacum

<400> SEQUENCE: 28
tttttttgga atatcaggtt tgg                                        23

<210> SEQ ID NO 29
<211> LENGTH: 23
<212> TYPE: DNA
<213> ORGANISM: Nicotiana tabacum

<400> SEQUENCE: 29
tttttttgga atatcatgtt tgg                                        23

<210> SEQ ID NO 30
<211> LENGTH: 23
<212> TYPE: DNA
<213> ORGANISM: Nicotiana tabacum

<400> SEQUENCE: 30
tttttttgga atatcaggtt tgg                                        23

<210> SEQ ID NO 31
<211> LENGTH: 23
<212> TYPE: DNA
<213> ORGANISM: Nicotiana tabacum

<400> SEQUENCE: 31
tttttttgga atatcatgtt tgg                                        23

<210> SEQ ID NO 32
<211> LENGTH: 23
<212> TYPE: DNA
<213> ORGANISM: Nicotiana tabacum

<400> SEQUENCE: 32
tttttttgga atatcaggtt tgg                                        23

<210> SEQ ID NO 33
<211> LENGTH: 23
<212> TYPE: DNA
<213> ORGANISM: Nicotiana tabacum

<400> SEQUENCE: 33
tttttttgga atatcatgtt tgg                                        23

<210> SEQ ID NO 34
<211> LENGTH: 23
<212> TYPE: DNA
<213> ORGANISM: Nicotiana tabacum

<400> SEQUENCE: 34
tttttttgga atatcaggtt tgg                                        23

<210> SEQ ID NO 35
<211> LENGTH: 23
<212> TYPE: DNA
<213> ORGANISM: Nicotiana tabacum

<400> SEQUENCE: 35
```
cttggagctg aagaggaaga agg                                                    23

<210> SEQ ID NO 36
<211> LENGTH: 21
<212> TYPE: DNA
<213> ORGANISM: Nicotiana tabacum

<400> SEQUENCE: 36
cttggagctg agaggagaag g                                                      21

<210> SEQ ID NO 37
<211> LENGTH: 22
<212> TYPE: DNA
<213> ORGANISM: Nicotiana tabacum

<400> SEQUENCE: 37
cttggagctg aagaggagaa gg                                                     22

<210> SEQ ID NO 38
<211> LENGTH: 21
<212> TYPE: DNA
<213> ORGANISM: Nicotiana tabacum

<400> SEQUENCE: 38
cttggagctg aagaggaaag g                                                      21

<210> SEQ ID NO 39
<211> LENGTH: 22
<212> TYPE: DNA
<213> ORGANISM: Nicotiana tabacum

<400> SEQUENCE: 39
cttggagctg aagaggagaa gg                                                     22

<210> SEQ ID NO 40
<211> LENGTH: 21
<212> TYPE: DNA
<213> ORGANISM: Nicotiana tabacum

<400> SEQUENCE: 40
cttggagctg agaggagaag g                                                      21

<210> SEQ ID NO 41
<211> LENGTH: 15
<212> TYPE: DNA
<213> ORGANISM: Nicotiana tabacum

<400> SEQUENCE: 41
cttggagctg aagag                                                             15

<210> SEQ ID NO 42
<211> LENGTH: 22
<212> TYPE: DNA
<213> ORGANISM: Nicotiana tabacum

<400> SEQUENCE: 42
cttggagctg aagaggagaa gg                                                     22

<210> SEQ ID NO 43
<211> LENGTH: 15
<212> TYPE: DNA
<213> ORGANISM: Nicotiana tabacum

<400> SEQUENCE: 43

-continued

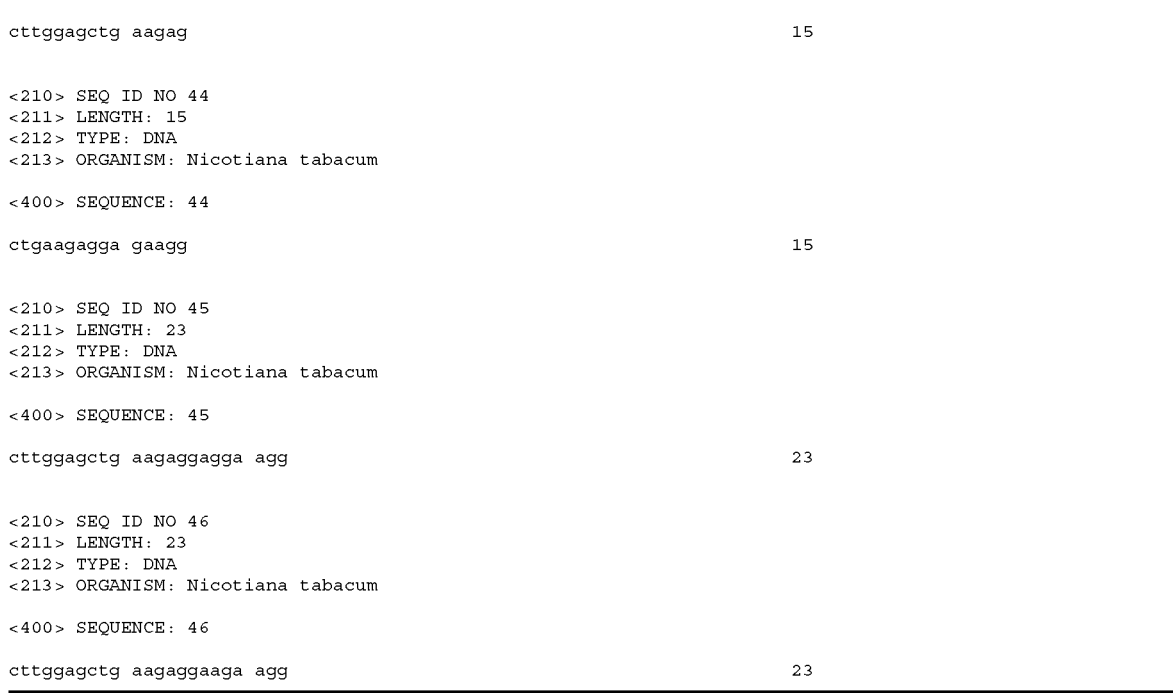

```
cttggagctg aagag                                                    15

<210> SEQ ID NO 44
<211> LENGTH: 15
<212> TYPE: DNA
<213> ORGANISM: Nicotiana tabacum

<400> SEQUENCE: 44
ctgaagagga gaagg                                                    15

<210> SEQ ID NO 45
<211> LENGTH: 23
<212> TYPE: DNA
<213> ORGANISM: Nicotiana tabacum

<400> SEQUENCE: 45
cttggagctg aagaggagga agg                                           23

<210> SEQ ID NO 46
<211> LENGTH: 23
<212> TYPE: DNA
<213> ORGANISM: Nicotiana tabacum

<400> SEQUENCE: 46
cttggagctg aagaggaaga agg                                           23
```